(12) United States Patent
Petrocelli

(10) Patent No.: US 7,277,903 B2
(45) Date of Patent: Oct. 2, 2007

(54) METHOD AND APPARATUS FOR DISTRIBUTED DATA ARCHIVING

(75) Inventor: Robert R. Petrocelli, Wakefield, RI (US)

(73) Assignee: Heartlab, Inc., Westerly, RI (US)

(*) Notice: Subject to any disclaimer, the term of this patent is extended or adjusted under 35 U.S.C. 154(b) by 158 days.

(21) Appl. No.: 09/920,973

(22) Filed: Aug. 2, 2001

(65) Prior Publication Data

US 2002/0046215 A1    Apr. 18, 2002

Related U.S. Application Data

(60) Provisional application No. 60/228,631, filed on Aug. 29, 2000.

(51) Int. Cl.
*G06F 17/30* (2006.01)
*G06F 17/00* (2006.01)

(52) U.S. Cl. .................. 707/204; 707/10; 707/104.1
(58) Field of Classification Search ........... 707/1–10, 707/100–104.1, 200–206; 705/2–4
See application file for complete search history.

(56) References Cited

U.S. PATENT DOCUMENTS

| | | | |
|---|---|---|---|
| 5,053,948 A | * | 10/1991 | DeClute et al. ............ 707/200 |
| 5,537,585 A | * | 7/1996 | Blickenstaff et al. ....... 707/205 |
| 6,199,072 B1 | * | 3/2001 | Jian et al. ................... 707/204 |
| 6,349,373 B2 | * | 2/2002 | Sitka et al. ................. 707/204 |
| 6,574,629 B1 | * | 6/2003 | Cooke et al. ................. 707/10 |
| 6,606,171 B1 | * | 8/2003 | Renk et al. ................. 358/475 |
| 6,763,523 B1 | * | 7/2004 | Sacilotto et al. ............. 725/91 |

* cited by examiner

*Primary Examiner*—Joon Hwan Hwang
(74) *Attorney, Agent, or Firm*—Houston Eliseeva LLP

(57) ABSTRACT

An archive system is provided for long term storage of large amounts of data that is particularly suited for multi-year storage of medical data such as cardiac images, patient demographics and reports. One or more digital versatile disks (DVDs) may be employed as the storage media. In the archival process, all of the data for a particular patient, procedure or study is stored and uniquely identified within one DVD. Each DVD may have an executable program stored thereon for independently accessing the archived data from the selected DVD. Before the DVD is recorded, the data to be archived is segmented into a plurality of information groups where each group is based on data for the particular patient, procedure or study. Then, the DVD is reviewed to determine whether a sufficient amount of storage space is present to ensure that the information group will be entirely stored within one DVD.

32 Claims, 5 Drawing Sheets

METHOD AND APPARATUS FOR DISTRIBUTED DATA ARCHIVING

CROSS REFERENCE TO RELATED APPLICATIONS

This application claims priority under 35 U.S.C. §119(e) to provisional patent application Ser. No. 60/228,631 filed Aug. 29, 2000, the disclosure of which is hereby incorporated by reference.

BACKGROUND OF THE INVENTION

The diagnosis and treatment of cardiac disease requires the acquisition of large amounts of data about the patient's medical condition. This data typically consists of medical images, patient information and clinical reports. The treatments of a single patient's disease can generate 1,000,000,000 bytes (1 Gbyte) or more of digital information. Millions of patients are treated worldwide each year for cardiac disease. Many other medical conditions exist for which similar quantities of data are maintained. The storage and management of such patient data requires more capacity than can be cost effectively deployed using standard magnetic disk technology.

The standard industry solution to this problem has been to combine small amounts of hard disk storage with large amounts of low cost magnetic tape storage. This combination of storage technology is implemented as a storage hierarchy. The premise of such a system is that newer data is accessed more frequently than old data. The typical Hierarchical Storage Management (HSM) system software used to manage a storage hierarchy moves data from the more costly hard disk storage to tape storage based on heuristics such as age of the data or last access time. HSM supports this type of data flow transparently to the software application that generates the data. In other words, if the data were a word processed document called mydoc.doc, access to a document is achieved by opening the file mydoc.doc. The HSM system provides access to data by restoring the data from tape to disk automatically. This transparency is created by a virtual file system (VFS). The VFS concatenates all of the storage in the hierarchy into one logical disk drive. The only apparent difference to the user is speed of access; files on the hard disk are accessed very quickly while files on the tape library are accessed with lengthy delays.

The transparency created by HSM creates problems due to monolithic access, proprietary formats, replication difficulties, and poor performance which make HSM poorly suited to mission critical medical image storage environments. Specifically, the primary design principle of HSM is to create transparency so that existing software does not need to be rewritten to take advantage of the large storage system. The transparency is achieved by aggregating all individual storage units (single tapes in a robotic library system plus hard disk(s)) into a single file system. As a result, files will be spread across all of the storage units in the hierarchy.

This design creates a situation where an individual storage unit is only meaningful in the context of the HSM system, which created it. Therefore, if a tape is removed from an HSM managed library, the tape will have no meaning outside of this HSM managed library and the tape must be restored to the HSM system to be accessed. HSM manufacturers often use proprietary or limited logical formats on each storage unit so that tapes cannot be read without the HSM software.

Although HSM often has a system for routine backup, HSM is viewed as a separate function from the backup and recovery management needed in the event of a catastrophe. As a result, HSM systems fail to provide for the creation of offsite copies of tapes for efficiently recreating the HSM in the event of a disaster. The complex data flow in HSM that moves files back and forth between levels in the hierarchy results in poor performance. An application must wait for a file to be fully restored from tape to disk before accessing the first byte of information.

BRIEF SUMMARY OF THE INVENTION

The archive system according to the present invention provides long term storage for large amounts of data. This system is particularly suited for multi-year storage of medical data such as cardiac images, patient demographics and reports. In a preferred embodiment, the archive system of the present disclosure employs one or more digital versatile disks (DVDs) as the storage media. In the archival process, all of the data for a particular patient, procedure or study is stored within one DVD and each DVD is uniquely identified. Also, each DVD may have an executable program stored thereon for independently accessing the archived data from the selected DVD.

Before all of the data is archived, the present archive system segments the data into a plurality of information groups where each group is based on data for the particular patient, procedure or study. Once the information groups are formed, each group is stored on a storage medium (DVD). Before recording an information group on a DVD, the DVD is reviewed to determine whether a sufficient amount of storage space is present to ensure that the information group will be entirely stored within one DVD. Once a DVD is found with enough storage capacity, the information group is stored thereon. This process is repeated for each information group. Although other storage media may be used, DVDs are preferable because their storage capacity is sufficient to store at least one typical information group.

In addition to the one or more information groups stored on each DVD, the unique identification and executable programs stored thereon allow each DVD or subsets of DVDs to be accessed independent from the other DVDs for viewing and printing the data on other processors or work stations. Also, the data from DVDs or DVD subsets created by different processors may be merged and modified to create new information groups.

BRIEF DESCRIPTION OF THE SEVERAL VIEWS OF THE DRAWING

The invention will be more fully understood by reference to the following detailed description of the invention in conjunction with the drawings, of which.

DETAILED DESCRIPTION OF THE INVENTION

To provide the storage of large amounts of data in the archive system according to the embodiments of the present invention, the data is segmented into information groups and stored onto archival storage media. For instance, data may be accessed from one or more external source(s) and segmented into information groups based on a desired procedure, study or patient.

Figure 1:
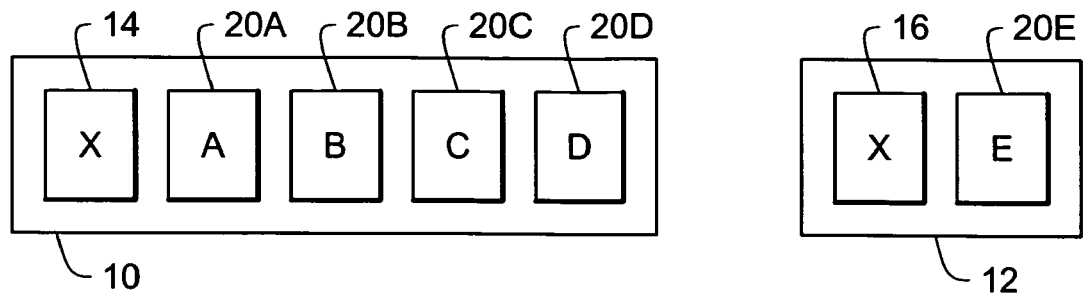
FIGS. 1(a)-1(d) illustrate configurations for the archival storage media according to embodiments of the present invention.
Figure 1:
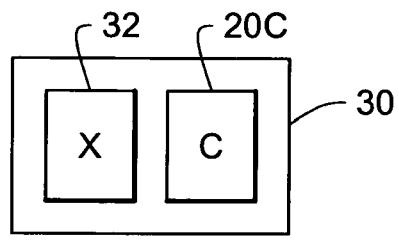
Figure 1:
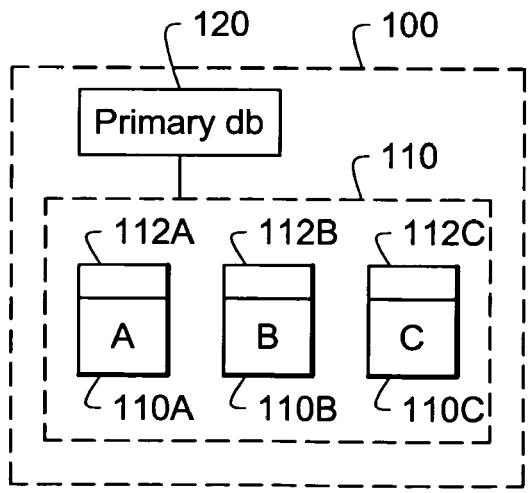
Figure 1:
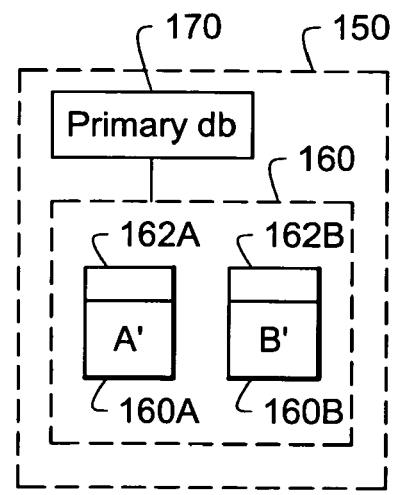

FIGS. 1(a)-1(b) illustrate configurations for storing such information groups in archival storage media by the present archive system. In FIG. 1(a), retrieved data segmented into information groups 20A, 20B, 20C, 20D, and 20E are recorded onto archival storage media 10 and 12. Four of the information groups 20A, 20B, 20C, and 20D and an index file 14 including an identifier, a database file, a data program, an image player, and/or other programs files are recorded on the archival storage medium 10 before a predetermined storage capacity is reached on the medium 10. The index file 14 allows the information groups 20A, 20B, 20C, and 20D stored on the archival storage medium 10 to be accessed, processed and viewed on a wide range of personal computers and operating systems.

The archival storage medium 10 is preferably a DVD, which is capable of storing one or more information groups. However, other archival storage media may be used as long as sufficient capacity is provided for storing at least one information group.

Before recording an information group, the recording processor determines whether the entire information group is able to be stored on the medium without exceeding its storage capacity. In the present illustrative example of FIG. 1(a), the four information groups 20A, 20B, 20C, and 20D are recorded onto the archival storage medium 10 without exceeding its storage capacity. In this example, the information group 20E cannot be recorded on the archival storage medium 10 without exceeding its storage capacity. Therefore, the information group 20E and an index file 16 including an identifier, a database file, a data program, an image player, and/or other programs files are recorded on the archival storage medium 12 as long as its storage capacity is not exceeded. The index file 16 allows the information group 20E to be accessed, processed, and viewed independently. This system and storage configuration ensures that each information group and the necessary programs and files to retrieve and view the respective information are entirely stored within one archival storage medium. As a result, each archival storage medium stands alone and is capable of being utilized independent from the other archival storage media so that its information can be accessed, viewed and processed.

The present archive system also allows for information and subsets of information stored on one or more disks to be accessed and merged to form new information groups. For instance, the information group 20C from the archival storage medium 10 can be accessed and recorded onto another archival storage medium 30 as illustrated in FIG. 1(b). Similar to the above described archival storage media, an index file 32 is recorded on the archival storage medium 30 to include an identifier, a database file, a data program, an image player, and/or other programs files for accessing, processing and viewing the information group 20C.

Figure 2:
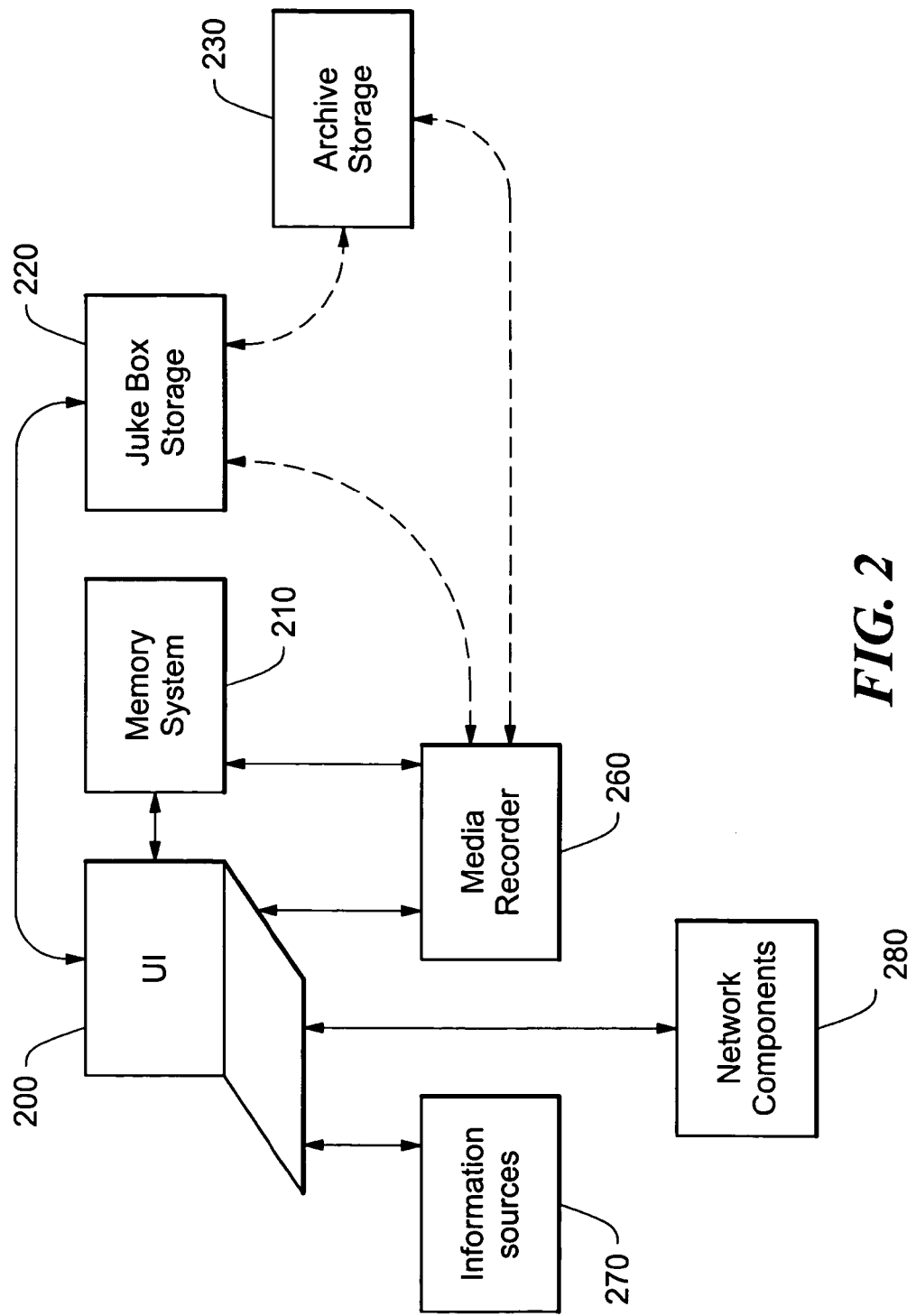
FIG. 2 illustrates an archival system according to an embodiment of the present invention.

FIG. 2 illustrates an archive system according to one embodiment of the present invention. A user interface (UI) 200 controls the present system for retrieving or receiving information from one or more source(s) 270. The UI 200 may be a conventional personal computer and the information source(s) 270 may be any type of device or component that supplies the desired data or information in a readable form to the UI 200. The archive system may be connected with network components 280, such as workstations, UIs, information sources and other network compatible devices. For example, when the desired data is in the medical environment, the information source(s) 270 may be a readable compact disk (CD) of patient reports or image data (such as CT, MR, CR, X-Ray Angiography and rf, PET, NM, US for example) images from scanners, X-Ray machines and the like.

The UI 200 communicates with a memory system 210 and a media recorder 260 for storing and recording the information from the information source(s) 270. The memory system 210 may be a hard disk, redundant array of independent disks (RAID), or external memory devices that are supported by the UI 200. The memory system 210 provides on-line storage for the initial creation of information file based on the data transfer from the information source(s) 270. The on-line information stored in the memory system 210 may be later accessed by the UI 200 based on universal naming convention (UNC) path of the memory system 210. The media recorder 260 is dependent upon the type of archival storage media that is used. When DVDs are used as the archival storage media, the media recorder 260 is a DVD recorder that is supported by the UI 200. After the DVDs are recorded, they may be physically placed in jukebox storage 220 as represented by the dashed line.

Due to the storage limitations of the memory system 210, a jukebox storage 220 is provided for retaining selected ones of the archival storage media. The UI 200 supports and communicates with the jukebox storage. Before the memory system 210 reaches its storage capacity, the media recorder 260 records one or more information groups onto at least one archival storage medium, such as a DVD. After the DVDs are recorded, they are mounted in the jukebox storage 220 such that the information on the DVDs are in "near-line" storage. Thereafter, the information on a DVD mounted in the jukebox storage 220 can be accessed by the UI 200 based on the UNC path of the DVD within the jukebox storage 220. One or more jukebox storage units may be incorporated into a single archive system.

Information may be present in the on-line and near-line state at the same time. When near-line information is deleted, the near-line state ends for that particular information. However, such near-line information will not be deleted but will receive an "end" date when the information is no longer valid.

Archive storage 230 is provided for off-line storage of the DVDs. The archive storage 230 may be shelf-type storage remote from the rest of the system. The archive storage 230 may include either duplicate copies of DVDs mounted in the jukebox storage 220 so that the information appears in both near-line and off-line states or DVDs that are removed from the jukebox storage 220 and are present only in the archive storage 230. The DVDs are physically placed in the archive storage from either the jukebox storage 220 or the media recorder 260 as represented by the dashed lines. Alternatively, some form of robotic manipulator may be employed to exchange archival storage media between "near-line" and "off-line" status. When the information contained on an off-line DVD is attempted to be accessed by the UI 200, a volume label of the DVD that was removed or copied from the jukebox storage 220 will result, indicating its "off-line" status.

The present archive system allows for a virtual archive 100 to be provided as illustrated in FIG. 1(c). The virtual archive 100 may include a set 110 of information groups 110A, 110B, and 110C that are in combinations of on-line, near-line, and off-line states. In one example, information group 110A is stored on-line and information groups 110B and 110C are stored near-line. In this case, a primary database 120 is stored in a separate medium from the other information groups 110A, 110B, and 110C of the virtual archive 100. Within each of the information groups 110A, 110B, and 110C, local databases 112A, 112B, and 112C are respectively stored. The primary database 120 has a database file for the constituent information groups of the virtual archive 100 to all of the local databases 112A, 112B, and 112C, the status of the storage media, the recorded time of the storage media, the type of data in the storage media, and other descriptive references relating to this virtual archive 100. Thereby, all of the related information groups 110A, 110B, and 110C can be readily accessed and retrieved despite being retained in different storage states.

The virtual archive 100 may be merged and modified as illustrated in FIG. 1(d). In this example, two information groups 110A and 110B may be retrieved from the virtual archive 100 to create another virtual archive 150. A set 160 of information groups 160A and 160B is created as duplicates or subsets from the information groups 110A and 110B. As above, the virtual archive 150 includes a primary database 170 for relating local databases 162A and 162B contained within the information groups 160A and 160B and retained in different storage states. Accordingly, the virtual archive 150 includes the information groups 160A and 160B while the information groups 110A, 110B, and 110C in the virtual archive 100 remain intact.

When the media recorder 260 records a DVD, a unique identifier is encoded thereon. This identifier uniquely identifies each DVD so that a DVD can be tracked, managed, and interchanged at different locations. Thereby, DVDs from one archive system can be transparently accessed and/or merged with DVDs from another archive system. In one embodiment, the unique identifier is a concatenation of a distinctly assigned volume label followed by values representing the recorded year, day within the year, hour, minute within the hour, seconds, and milliseconds. For example, a DVD assigned a volume label of 1.2.840.113815 on Sep. 22, 1999 at 9:12:46.157 AM would have the following identifier:

1.2.840.113815.1999265091246157.

In this example, no two primary DVD copies will have the same identifier. The identifier is machine-readable and conforms to the universal disk format (UDF) standard volume label format for removable media.

Each DVD also includes a self-contained database file for holding all of the meta-data required to completely describe a procedure or study stored on that DVD. For instance, in the medical environment, the self-contained database may include all of the demographics for a patient required to adequately review the clinical procedures, stored on that medium. Digital Image Communications for Medicine (DICOM-3) is preferably used to implement this database file. DICOM-3 is a known standard for enhancing the ability of medical imaging devices and equipment to transfer medical images and information between systems, such as between a computer tomography (CT) scanner, a workstation, and a printer.

By requiring each information group or the information for each patient to be entirely contained on one storage medium or DVD, it is possible to utilize the self-contained database file for independently accessing, viewing, and processing each DVD. This addresses a deficiency associated with conventional HSM based systems using DICOM-3, with which patient data often spans two media, such as two magnetic tape units. Each DVD may be exchanged between archive systems without secondary database transactions to fully describe a procedure or study. Also, standard clinical imaging stations may directly read the DVDs, allowing review of archived images outside of the archive system in which it was originally created. This is in contrast to prior art systems in which the contents of one storage mechanism such as a magnetic tape are meaningless outside the context of the archive in which it was created. In the event of failure of the primary archive system according to the present invention, information from the DVD may be retrieved on a different archive system, computer, or imaging station.

System auditor data is also recorded on the DVDs for allowing information to be mounted in or removed from an archive system. Information from the DVD's comprising the archive is automatically synchronized to the primary information database whenever information is added to or read from a DVD. The system auditor allows DVDs from different archives to be combined to create a new archive with a single coherent primary database. When a DVD is removed from the system, the system auditor changes the location and status information for that DVD in the primary database to the off-line.

The archive system may also include software for automated network-based media duplication. This duplication software allows for the creation of exact duplicates of the DVDs stored in the archive system on a network attached thereto. Thereby, exact copies of primary archival storage media may be created and stored at different physical locations so that a complete restoration of the archived information may be performed in the event of a disaster. When using the duplication software in combination with the system auditor, an empty primary database may be completely rebuilt from information stored on archived storage media. If an archive system is completely destroyed, duplicate off-line media can be used to completely reproduce the original information system on a new archive system.

An embedded image player is also recorded on the DVDs in this example. The embedded image player includes a computer program for initiating the display of the meta-data, image data, and associated test results contained on the DVD. Thus, the patient data contained on the DVDs may be accessed and reviewed at any later time without specialized equipment or software.

The archive system selects information to be archived based on predefined system settings. These settings may include: archive oldest or newest first; the number of archival storage media to be written; media storage capacity; run time; media information staging directory; whether to write to the media or location to move files; and UNC path for study to identifier text file for tracking the media.

Figure 3:
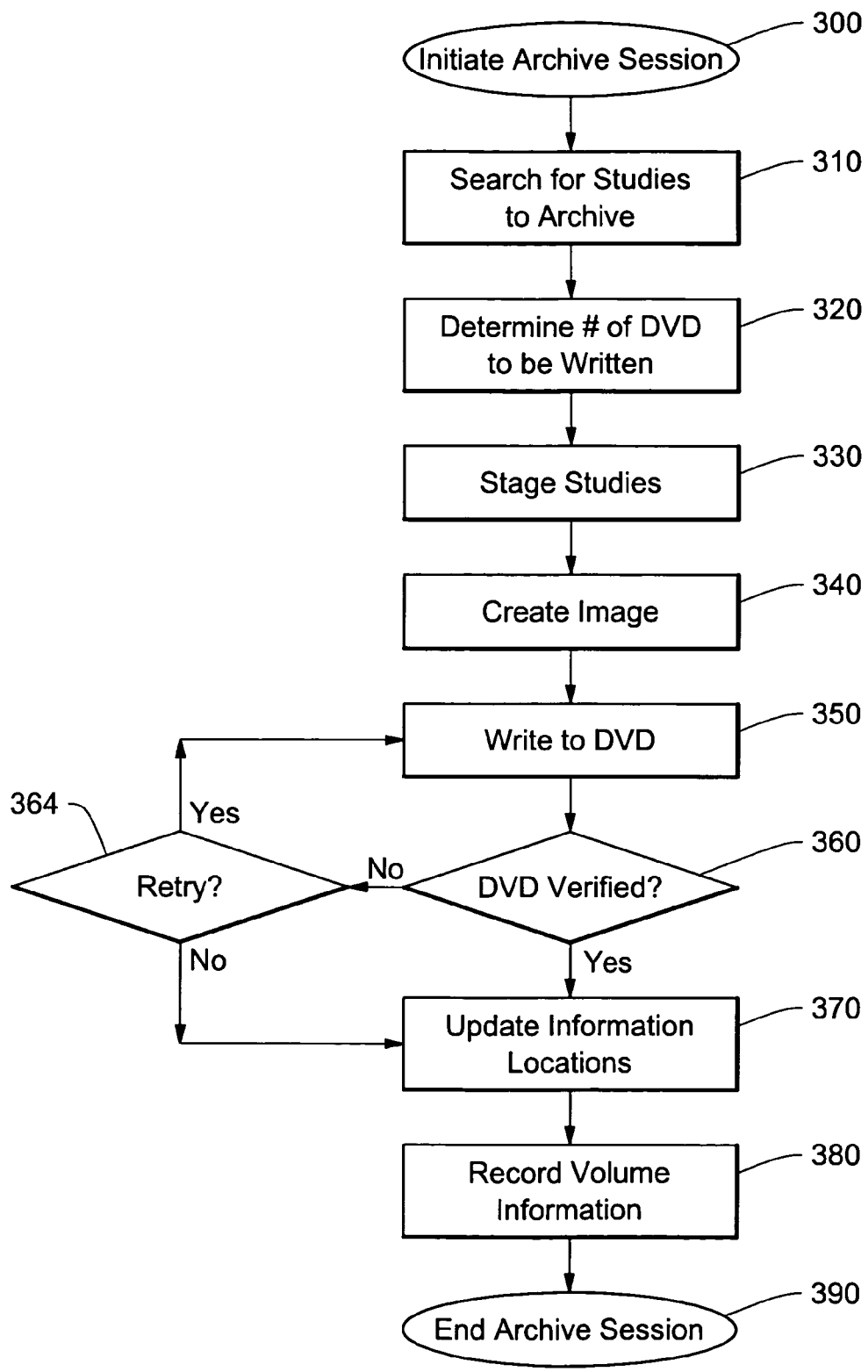
FIG. 3 is a flow chart of an archive session according to an embodiment of the present invention.

In one embodiment of the present archive system, the archiving process runs as a Windows NT service from the UI 200. The archiving process is configured to run without user interaction with provisions for manually starting, stopping, pausing, and continuing through the UI 200. An application may be provided to update the status of the archiving process. FIG. 3 is a flow chart illustrating an example of an archive session according to an embodiment of the present invention. The archive session is initiated at step 300. A search and compilation of studies or procedures are conducted at step 310. After the studies or procedures are obtained, the number of archival storage media or DVDs needed for these studies or procedures is established at step 320. The studies and/or procedures are staged and segmented into information groups at step 330 and any images are created at step 340. At step 350, the information groups are written on each DVD.

After writing one or more information groups on a DVD, that DVD is verified at step 360 as to whether the writing has been successfully completed. For example, verification determines whether each intended information group is contained within the DVD. If the DVD is not verified, it is determined whether writing to the DVD is to be retried at step 364. If a retry is desired or appropriate, writing to the DVD is repeated at step 350. If the DVD is verified or if a retry is not desired, the information group locations are updated at step 370. Next at step 380, the identifier and index files are recorded before the archive session ends at step 390.

Figure 4A:
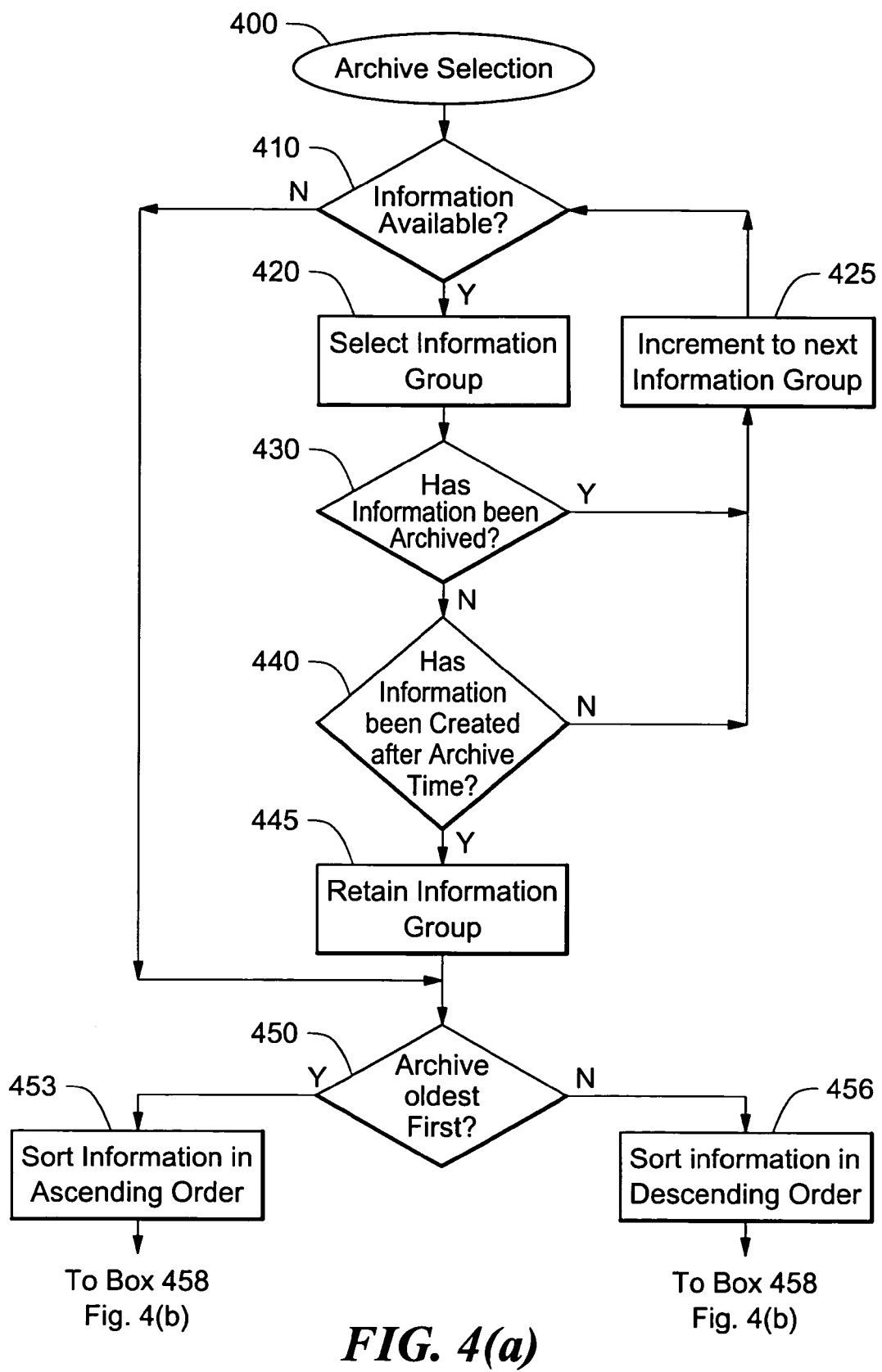
FIG. 4 is a flow chart of an archive selection according to an embodiment of the present invention.
Figure 4B:
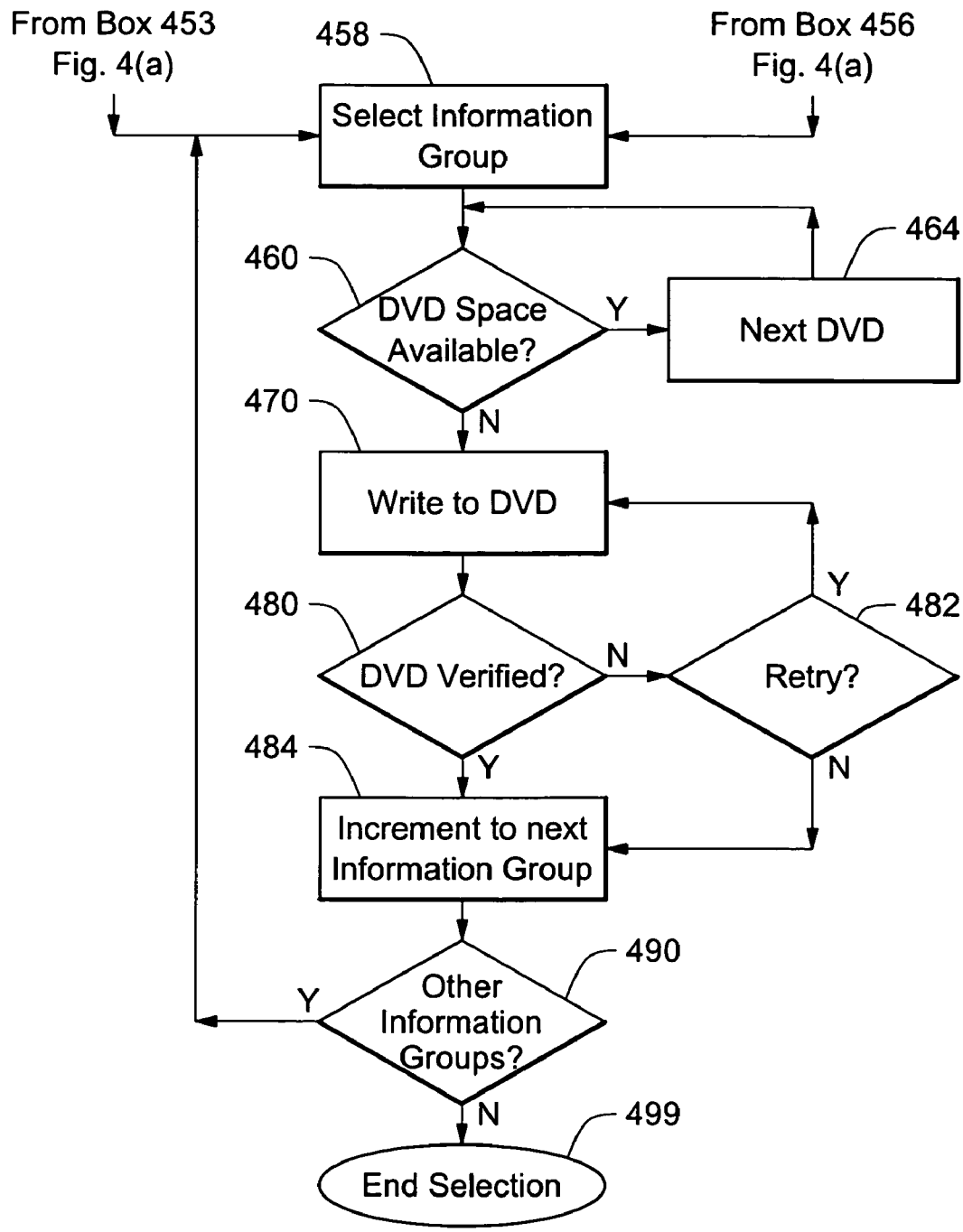

The archive session may be configured to start archiving at a specified time each day. When the archiving process starts, a number of specified DVDs are written as long as information is available based on a selection process in one embodiment of the present invention. As illustrated in FIG. 4, the present archive selection is initiated at step 400. At step 410, it is determined whether any information groups are available. One information group is selected at step 420 when it is determined to be available. At step 430, it is determined whether the selected information group has already been archived. If the selected information group has not been archived, it is determined whether this information group was created after an archive time setting has expired. This archive time setting is a predefined value corresponding to a desired minimum time to age before archiving is performed.

If the selected information group was created before the archive time setting expired or was previously archived, the process increments to the next information group, if available, at step 425 without storing the information group for further processing. If the selected information group was created after the archive time setting expired and was not previously archived, this information group is retained for further processing at step 445.

When no further information groups are determined to be available at step 410, the archiving order is determined at step 450. If the archiving process is configured to archive the oldest information groups first, the information groups are sorted in ascending order by date and time at step 453. Otherwise, the archiving process is configured to archive the oldest information groups last and the information groups are sorted in descending order by date and time at step 456. Other metrics may be used to define the archive order.

The first of the sorted information group is selected at step 458 and the amount of available storage capacity for a selected DVD is compared to the selected information group. The available storage capacity is determined by using a predefined percentage full value for the DVD. The amount of storage capacity remaining if the information group were to be recorded onto the DVD is compared to the percentage full value. The information group is recorded onto the DVD at step 470 if the percentage full value of the DVD will not be exceeded. However, if recording the information group onto the selected DVD would exceed the percentage full value, another DVD is selected at step 464 and then the available storage capacity of the new DVD is determined. Accordingly, the information group will not span across two or more DVDs and each information group will be entirely contained within one DVD.

Verification of writing to the DVD is performed at step 480. If writing of the information group is not verified, it is determined whether a retry of writing the information group is desired at step 482. If the information group recorded onto the DVD is verified at step 480, the process attempts to increment to the next information group at step 484 and determines whether another information group is available at step 490. If another information group is available, the next information group is selected at step 458. However, if no more information groups are determined to be available at step 490, the archive selection ends at step 499.

It will be apparent to those skilled in the art that other modifications to and variations of the above-described techniques are possible without departing from the inventive concepts disclosed herein. Accordingly, the invention should be viewed as limited solely by the scope and spirit of the appended claims.

What is claimed is:

1. A method for distributed data archiving, comprising the steps of:

accessing patient medical data from at least one external source;

segmenting the patient medical data into a plurality of information groups with each information group corresponding to information about a particular patient;

providing a data archiving system comprised of a plurality of archival storage media;

storing each information group onto an archival storage media, said information groups being stored on said archival storage media with each information group having an identification, the identification being unique from all other information groups stored within said archival storage media and all other archival storage media, enabling said information groups to be independently accessed, within or without the data archiving system in which the information groups were created, and each information group being stored entirely only on one of said plurality of archival storage media by the following steps:

determining an available storage capacity of the storage medium, comparing the available storage capacity of the storage medium to the information group that is to be stored, recording the information group on the selected storage medium only if a size of the information group is smaller than the available storage capacity of the storage medium, and selecting another storage medium if the size of the information group is larger than the available storage capacity of the storage medium;

encoding a unique identifier on said one of said plurality of archival storage media to uniquely identify the storage medium from all other storage media, said encoding step including recording an index file having at least an identifier, a data program, and a self-contained database file for each of said information groups on said one of said plurality of archival storage media, wherein the database file recorded on the archival storage media contains information describing clinical procedures of the patient medical data stored on the archival storage media, and wherein the database file is implemented by Digital Image Communications for Medicine; and independently accessing said one of said plurality of archival storage media at a site other than said data archiving system by reading said index file.

2. A method according to claim 1, wherein said archival storage media comprise digital versatile disks (DVDs).

3. A method according to claim 1, wherein said information groups comprise meta-data and image data.

4. A method according to claim 3, wherein each of said archival storage media comprises an embedded image player for viewing the images.

5. A method according to claim 3, wherein each of said archival storage media comprises an application for interpreting the meta-data.

6. A method according to claim 1, further comprising the step of creating an executable program on each of said archival storage media for retrieving said information groups stored thereon.

7. A method according to claim 1, further comprising the step of recording said information groups on said archival storage media as near-line and off-line storage.

8. A method according to claim 1, wherein a first subset of said archival storage media is provided as on-line storage.

9. A method according to claim 8, wherein said on-line storage comprises a hard disk.

10. A method according to claim 1, wherein a second subset of said archival storage media is provided as near-line storage.

11. A method according to claim 10, wherein said near-line storage comprises a jukebox storage for providing sequentially selectable access to at least one archival storage media.

12. A method according to claim 1, wherein a third subset of said archival storage media is provided as off-line storage.

13. A method according to claim 12, wherein said off-line storage comprises shelf storage for said archival storage media.

14. A method according to claim 1 including independently accessing said one of said plurality of archival storage media by accessing the archival storage media at a clinical imaging station allowing a review of archived images outside of the data archiving system in which the archival storage media was originally created.

15. A method according to claim 1 including encoding an index file that also has an image player.

16. A method according to claim 15 wherein the database file holds all of meta-data required to completely describe a procedure or study stored on the archival storage media.

17. A method according to claim 1 wherein the identifier comprises a volume label.

18. A method according to claim 1, wherein the database file further contains patient demographic information relevant to the clinical procedures recorded on the archival storage media.

19. A distributed data archiving system, comprising:
a user interface for controlling the system, said user interface including a processor for receiving patient medical data from a plurality of external sources and segmenting the patient medical data into a plurality of information groups; and
a memory storage comprised of a plurality of separate archival storage media for storing information groups with each information group corresponding to information about a particular patient, each information group being stored entirely only on one of said plurality of archival storage media by determining an available storage capacity of the storage medium, comparing the available storage capacity of the storage medium to the information group that is to be stored, recording the information group on the selected storage medium only if a size of the information group is smaller than the available storage capacity of the storage medium, and selecting another storage medium if the size of the information group is larger than the available storage capacity of the storage medium,
each archival storage media comprising: 1) a group information identification, the group information identification being unique from all other information groups stored within said archival storage media and all other archival storage media; 2) a unique identifier to uniquely identify the archival storage media from all other archival storage media; and 3) an index file having a data program and a self-contained database file, for each of said information groups, containing information describing clinical procedures of the information groups stored on the archival storage media, said information groups are independently accessed, within or without the data archiving system in which the information groups were created, wherein the database file is implemented by Digital Image Communications for Medicine, and wherein the archival storage media is independently accessed at a site other than said data archiving system by reading said index file.

20. A distributed data archiving system according to claim 19, wherein said user interface comprises a personal computer.

21. A distributed data archiving system according to claim 19, wherein said external sources comprises a workstation.

22. A distributed data archiving system according to claim 19, wherein said external sources comprises a network compatible device.

23. A distributed data archiving system according to claim 19, wherein said memory storage comprises on-line, near-line, and off-line storage media.

24. A distributed data archiving system according to claim 23, wherein said on-line storage media comprises a hard disk.

25. A distributed data archiving system according to claim 23, wherein said on-line storage media comprises a redundant array of independent disks.

26. A distributed data archiving system according to claim 23, wherein said near line storage media comprises a jukebox storage for providing sequentially selectable access to said archival storage media.

27. A distributed data archiving system according to claim 23, wherein said off-line storage media comprises shelf storage for said archival storage media.

28. A distributed data archiving system according to claim 23, further comprising a media recorder for recording said information groups on said archival storage media as near-line and off-line archival storage media.

29. A distributed data archiving system according to claim 19, wherein said user interface creates an executable program for retrieving said information groups stored on said archival storage media and stores said executable program on said archival storage media.

30. A distributed data archiving system according to claim 19, wherein said archival storage media comprise digital versatile disks (DVDs).

31. A distributed data archiving system according to claim 19 wherein the same information group is stored on more than one storage medium having a different unique identifier associated with each.

32. A distributed data archiving system according to claim 19, wherein the database file further contains patient demographic information relevant to the clinical procedures recorded on the archival storage media.

* * * * *